(12) United States Patent
Hayden et al.

(10) Patent No.: US 9,605,293 B2
(45) Date of Patent: Mar. 28, 2017

(54) METHOD FOR DETECTING A PLASMODIUM INFECTION

(75) Inventors: Oliver Hayden, Herzogenaurach (DE); Jan van den Boogaart, Someren (NE)

(73) Assignee: SIEMENS HEALTHCARE DIAGNOSTICS PRODUCTS GMBH, Marburg (DE)

( * ) Notice: Subject to any disclaimer, the term of this patent is extended or adjusted under 35 U.S.C. 154(b) by 0 days.

(21) Appl. No.: 13/996,948

(22) PCT Filed: Dec. 20, 2011

(86) PCT No.: PCT/EP2011/073428
§ 371 (c)(1),
(2), (4) Date: Aug. 29, 2013

(87) PCT Pub. No.: WO2012/084963
PCT Pub. Date: Jun. 28, 2012

(65) Prior Publication Data
US 2013/0337496 A1    Dec. 19, 2013

(30) Foreign Application Priority Data

Dec. 23, 2010 (DE) .................. 10 2010 064 131
Jan. 25, 2011 (DE) .................. 10 2011 003 101

(51) Int. Cl.
| | |
|---|---|
| C12Q 1/04 | (2006.01) |
| C12Q 1/02 | (2006.01) |
| G01N 15/14 | (2006.01) |
| G01N 15/00 | (2006.01) |

(52) U.S. Cl.
CPC ............ *C12Q 1/04* (2013.01); *C12Q 1/02* (2013.01); *G01N 15/1456* (2013.01); *G01N 2015/008* (2013.01); *G01N 2333/445* (2013.01)

(58) Field of Classification Search
CPC ...... C12Q 1/04; C12Q 1/02; G01N 2015/008; G01N 2015/0084; G01N 2333/445
USPC ............................................. 435/34
See application file for complete search history.

(56) References Cited

U.S. PATENT DOCUMENTS

| | | | |
|---|---|---|---|
| 5,045,472 A | 9/1991 | Ornstein et al. | |
| 5,284,771 A | 2/1994 | Fan et al. | |
| 5,633,167 A | 5/1997 | Fan et al. | |
| 5,888,752 A | 3/1999 | Shapiro | |
| 6,114,173 A | 9/2000 | Zelmanovic et al. | |
| 2006/0250604 A1 | 11/2006 | Ueno | |
| 2011/0053210 A1 | 3/2011 | Itose | |

FOREIGN PATENT DOCUMENTS

| | | | |
|---|---|---|---|
| EP | 0545313 A1 | 6/1993 | |
| JP | H06180316 A | 6/1994 | |
| JP | H08313518 A | 11/1996 | |
| JP | 2006313151 A | 11/2006 | |
| JP | 2007525674 A | 9/2007 | |
| WO | WO 2005088301 A1 | 9/2005 | |
| WO | WO 2009136570 A1 | 11/2009 | |

OTHER PUBLICATIONS

Buss et al. Occurrence, Etiology, and Clinical Significance of Extreme Thrombocytosis: A Study of 280 Cases; The American Journal of Medicine, vol. 96 (1994) pp. 247-253.*
Grinstein et al. Volume Changes in Activated Human Neutrophils: The Role of Na+/H+ Exchange; Journal of Cellular Physiology, vol. 128 (1986) pp. 33-40.*
Osselaer et al. Platelet Distribution Width for Differential Diagnosis of Thrombocytosis; Clincal Chemistry, vol. 43, No. 6 (1997) pp. 1072-1076.*
Papakonstantinou et al. Mean Neutrophil Volume: A New Automated Hematologic Parameter for Acute Infection; 13th Congress of the European Hematology Association, Jun. 12-15, 2008, downloaded from http://www.online.haematologica.org/eha13/browserecord_prt.php?-action=browse&-recid=2530 on Jun. 16, 2014.*
Worthen et al. Neutrophils Increase Volume During Migration in Vivo and in Vitro; American Journal of Respiratory Cell and Molecular Biology, vol. 10 (1994) pp. 1-7.*
Kotepui et al. Effect of Malarial Infection on Haemotological Parameters in Population Near Thailand-Myanmar Border; Malaria Journal, vol. 13, No. 218 (2014) pp. 1-7.*
Muwonge et al. How Reliable Are Hematological Parameters in Predicting Uncomplicated Plasmodium Falciparum Malaria in an Endemic Region?; ISRN Tropical Medicine, vol. 2013, article ID 673798 (2013) pp. 1-9.*
Canadian Medical Association Journal; A.Humar et al; "Fatal falciparum malaria in Canadian travellers"; Apr. 15, 1997; 156(8), pp. 1165-1167.
American Society for Clinical Pathology 2006; C. Briggs et al; "Development of an Automated Malaria Discriminant Factor Using VCS Technology", 2006, 126, pp. 691-698.
Emerging Infectious Diseases; T. Hanscheid et al.; "Avoiding misdiagnosis of malaria: a novel automated method allows specific diagnosis, even in the absence of clinical suspicion"; Nov.-Dec. 1999, vol. 5, No. 6, pp. 836-838.
Nature 2006; ME Rafael, T. Tylor, A. Magill et al.; Reducing the burden of childhood malaria in Africa: The role of improved diagnosis.; 444 (suppl 1): pp. 39-48.
Malaria Journal 2010; veröffentlichte Paper "Automated haematology analysis to diagnose malaria", 9:346.

(Continued)

*Primary Examiner* — Scott Long
*Assistant Examiner* — Paul Martin
(74) *Attorney, Agent, or Firm* — Dugan & Dugan, PC (57) ABSTRACT

The invention relates to a method for detecting a *plasmodium* infection in a patient blood sample, wherein a differential analysis of the polymorphonuclear neutrophil granulocytes in the sample is performed, and the distribution of the cell volume and the cell density, the number of thrombocytes in the sample, and the distribution of the cell density of the thrombocytes in the sample is determined.

10 Claims, 4 Drawing Sheets

(56) References Cited

OTHER PUBLICATIONS

Clinics in Infectious Diseases; Kain et al., 1998, 27, pp. 142-149.
"Automated haematology analysis to diagnose malaria"; Malaria Journal 2010; Campzano-Zuluaga G u.a.; "Automated haematology analysis to diagnose malaria"; Nov. 30, 2010; 9:346 pp. 1-15.
Clinical Chemistry 1985; Kim et al; "Subtyping Lymphocytes in Peripheral Blood by Immunoperoxidase Labeling and Light Scatter/Absorption Flow Cytometry"; Bd. 31, Nr. 9, Sep. 1, 1985, Seiten 1481-1486. XP55021365.
Umang, Patel et al.; "Thrombocytopenia in Malaria"; Journal of the national medical association, vol. 96, No. 9; pp. 1212-1214; (2004).
Yushu, Fan; "Hint of Plasmodium Infection by the Increase of Abnormal Granulocyte AC.T5diff Blood Analyzer"; pp. 4333-4334; (2010).

* cited by examiner

METHOD FOR DETECTING A PLASMODIUM INFECTION

PRIORITY STATEMENT

The present application hereby claims priority under 35 U.S.C. §119 of the European Patent Application Number DE102010064131.6, filed Dec. 23, 2010, DE102011003101.4 filed Jan. 25, 2011 and PCT/EP2011/073428 filed Dec. 20, 2011, the entire contents of which are hereby incorporated herein by reference.

FIELD OF THE INVENTION

The invention relates to a method for detecting a *plasmodium* infection in a patient blood sample.

BACKGROUND OF INVENTION

*Plasmodium* infections, such as malarial sicknesses caused for example by the pathogens *Plasmodium falciparum, Plasmodium vivax, Plasmodium ovale, Plasmodium malariae* and also *Plasmodium knowlesi*, are the cause of hundreds of millions of new infections worldwide per year. According to figures from the World Health Organization (WHO) the estimate of new infections per year ranges from 300 to 500 million people.

In respect of the increasing development of resistance to the existing medicines for treating *plasmodium* infections there is therefore an increasing demand for reliable, low-cost and quick-to-perform diagnostic methods, which can additionally largely exclude false-positive and false-negative results. For example highly-sensitive diagnostic methods would be necessary in regions with a low prevalence of malarial infections in order to recognize the few people with the illness as actually having it.

On the other hand, in regions of the world with a higher prevalence/incidence, which are usually among the poorer regions of the world, there is a high demand for test methods with a high specificity, in order to exclude false-positive results (i.e. also recognize healthy people as being healthy).

As a rule the problem also exists of not only an extremely high number of patient samples having to be examined, but of this—as discussed above—also having to be done quickly. This is because the results of the diagnosis should be available within less than 2 hours. If this is not possible the patient may possibly have to be treated on the basis of a superficial clinical analysis.

The results of an incorrect or false-negative/false-positive malaria diagnosis are wide-ranging: with a false-positive diagnosis the (pointless) use of medicines can be accompanied by avoidable side-effects, quite apart from the financial load on the healthcare system, as well as the possibility of the plasmodia building up resistance. In a study from the year 2006 it was concluded that a diagnostic test with the sensitivity and specificity of 95% in each case which only needs minimal infrastructure could save more than 100,000 deaths and more than 400 million unnecessary treatments (Rafael M E, Taylor T, Magill A et al. Reducing the burden of childhood malaria in Africa: The role of improved diagnosis. Nature. 2006; 444 (suppl 1): 39-48)

In practice the main problem arising in the diagnosis of parasitic illnesses, for example malaria, is that the laboratory diagnosis is only undertaken when a clinical suspicion arises that the patient is actually suffering from this type of infection. This can lead, especially in regions with a low prevalence/incidence, to persons with the illness not being treated or not being treated in good time. For example in a Canadian study (Kain et al, 1998, Clinics in Infectious Diseases 27, 142-149) it was reported that the correct diagnosis was not initially made for 59% of all travelers returning infected with malaria. On average 7.6 days elapsed before the correct diagnosis was made and before the beginning of therapy for *Plasmodium falciparum* and 5.1 days for *Plasmodium vivax*. These types of delays can lead to significant complications and to an increased mortality rate (Humare et al, 1997, *Canadian Medical Association Journal* 156, 1165-1167).

There are a number of methods available for the diagnosis of *plasmodium* infections: the safest method consists of a microscopic blood examination, however this method is very labor-, time- and equipment-intensive. With the conventional microscopic method trained expert personnel can reliably determine the type and the stage of the infection.

So-called Rapid Diagnostic Tests (RDT) also exist. For example monoclonal antibodies are used here for the verification of parasitic antigens. This test is usually used to detect *Plasmodium falciparum* infections.

A far more sensitive method for malaria diagnosis consists of the polymerase chain reaction which, because of the high outlay in materials and time however, is little suited to acute cases.

The group of Rapid Diagnostic Tests (RDT) has recently also come to include automated methods which, because of their high throughput, are outstandingly suitable for wide-area-coverage verification methods. Cf. Hanscheid T, Pinto B G, Pereira I, Christino J M, Valadas E (1999) Avoiding misdiagnosis of malaria: a novel automated method allows specific diagnosis, even in the absence of clinical suspicion. *Emerging Infectious diseases* [1999, 5(6): 836-838].

For automatic use so-called automated cell counters are being employed with increasing success. Examples of such counters are the Advia 2120, Sysmex XE-2100 and also CellaVision DM96. These automated devices, apart from their high throughput rate, provide a number of benefits, such as for example higher objectivity (no observer-dependent variability), elimination of statistical variations which are usually associated with manual counting (counting high cell numbers), as well as the determination of numerous parameters which would not be available during manual counting and, as mentioned, a more efficient and cost-effective treatment. A few of these devices can process between 120 and 150 patient samples per hour.

The technical principles of the automatic single cell counting are based either on an impedance measurement or on an optical system (scattered light or absorption measurement).

With the impedance method the counting of the cells and also the determination of their size is done on the basis of the detection and the measurement of changes in the electrical conductivity (impedance) which are caused by a particle which is moving through a small opening. Particles, such as blood cells for example, are not themselves conductive, but are suspended in an electrically-conductive thinning medium. If such a suspension of cells is passed through an opening, during the passage of a single individual cell the impedance of the electrical path between the two electrodes which are located on each side of the opening temporarily increases.

For example a method is described in WO 2005/088301 for verifying malaria and other parasitic infections by means of such an impedance measurement (see experimental part) and also in the article entitled "Development of an Automated Malaria Discriminant Factor Using VCS Technology", Briggs C et al. Am J Clin Pathol 2006.

By contrast with the impedance methods, the optical method comprises the passing of a laser light beam through a thinned blood sample which is detected in a continuous stream by the laser beam. Each cell which passes through the detection zone of the throughflow cells scatters the focused light. The scattered light is then detected by a photo detector and converted into an electrical impulse. The number of impulses generated here is directly proportional to the number of cells which pass through the detection zone within a specific period of time.

In the optical methods the light scattering of the individual cells which pass through the detection zone is measured at different angles. Information about cell structure, shape and reflection ability is detected through this. These properties can be used to differentiate between different types of blood cells and use the derived parameters for diagnosis of deviations of the blood cells from the norm.

The values obtained by the two measurement methods are logically linked by means of differential diagnostics into a meaningful diagnosis result.

The sensitivity and specificity of diagnostic methods plays a major role within the framework of differential diagnostics, accordingly work on improving these properties is constantly being undertaken.

For example in WO 2005/088301 the measured values relating to the cell volume of lymphocytes and monocytes are detected and included as parameters for a malarial disease. In more precise terms the standard deviation of the volumes of the monocyte and lymphocyte populations is assessed, i.e. their heterogeneity. It has transpired however that this parameter is not specific enough for the diagnosis of a parasitic infection, since other infectious diseases (for example colds) can also result in a change in volume of the lymphocytes and monocytes. In addition impedance measurements of blood samples have also proved to be susceptible to errors, e.g. measurement results can be falsified (for example by varying viscosity of the suspension to be tested).

In a similar manner a description is given in "Development of Automated Malaria Discriminant Factor Using VCS Technology" (see above) of how the standard deviation of the volume of lymphocytes and monocytes deviates significantly from the standard value when a malaria infection is present.

An example presentation of different sensitivities and specificities using automated blood test devices can be found in Table 3, in accordance with which the sensitivity in some cases only amounts to 48.6 or 52%. Success is thus not achieved to a sufficient extent with the conventional test methods in providing methods with high sensitivity and specificity, i.e. methods for detecting a *plasmodium* infection, which also recognize ill patients as such, as well as on the other hand being able to recognize a healthy patient as healthy.

In accordance with more recent investigations the expressiveness of the existing automated test systems (and thus also of the specified sensitivities/specificities) is also questionable and allows scope for improvements. In this connection see the recently published paper "Automated hematology analysis to diagnose malaria", Malaria Journal 2010, 9:346.

SUMMARY OF INVENTION

It is therefore an object of the present invention to provide a method for detecting a *plasmodium* infection in a blood sample which produces test results with higher sensitivity and specificity. It is a further object of the invention to provide a detection method for malaria infections which by the use of a number of independent parameters, allows a high specificity and sensitivity for malaria independently of other infections or different states of health of the patients. It is yet another object of the present invention to provide such a method which can be performed with the aid of automated blood analysis devices.

This object is inventively achieved by a method with the features claimed in claim 1.

The invention creates a method for detecting a *plasmodium* infection in a patient blood sample, comprising a) Performing a differential analysis of the polymorphonuclear neutrophil granulocytes in the sample and determining the distribution of the cell volume and the cell density;
b) Determining the number of thrombocytes in the sample;
c) Determining the distribution of the cell density of the thrombocytes in the sample;
d) Obtaining sample parameters from the values determined in steps a) to c); and
e) Assessment of the parameters against a prespecified criterion, wherein a *plasmodium* infection is present if the criterion is fulfilled.

BRIEF DESCRIPTION OF THE DRAWINGS

A more complete appreciation of the present invention and many of the attendant advantages thereof will be readily understood by reference to the following detailed description when taken in conjunction with the accompanying drawings, in which.

DETAILED DESCRIPTION OF INVENTION

The patient blood sample examined in accordance with the invention as a rule involves a human blood sample. It is however also possible to examine blood samples of mammals.

The term "differential analysis", as used herein, means the recording of a number of measurable individual values of the components of the patient blood sample which will ultimately be evaluated combined for the diagnosis to be performed.

In step a) of the inventive method, to perform this method, first of all a differential analysis of the polymorphonuclear neutrophil granulocytes in the sample is carried out in relation to determining the distribution of the cell volume and the cell density. However this does not exclude further leukocyte types, for example eosinophils or basophils also being included in an examination.

A deviation of the distribution of the cell volume as well as of the cell density from the norm normally point to a pathological state. In the present case, compared to the usually measured normal values, lower values point to a *plasmodium* infection. The reduction of the cell volume and of the cell density associated with the *plasmodium* infection is to be explained by the defense mechanisms of the leukocytes occurring during the course of the infection. For example neutrophil granulocytes migrate from the blood vessel into the tissue, secrete proteolytic enzymes there in order to release intercellular compounds and phagocytize bacteria there. This results in a change to the cell volume and the cell density.

It has surprisingly been shown that the sensitivity and specificity of the detection method for a *plasmodium* infection can be greatly increased if, as well as the values determined above (i.e. sequentially or simultaneously) both the thrombocyte number in the patient blood sample and also the distribution of the cell density of the thrombocytes in the sample is determined. Here too a value deviating downwards from the norm is predictive of the presence of a *plasmodium* infection. In accordance with the invention this leads to a greatly increased sensitivity and specificity of the detection method compared to existing methods.

From the measurement results obtained in steps a) to c) sample parameters are obtained and assessed in relation to a previously defined criterion, wherein a *plasmodium* infection is present if the criterion is fulfilled.

The parameters involve derived variables, for example the term cell volume parameter stands for a parameter related to the cell volume distribution such as for example the average cell volume or the standard deviation of the cell volume distribution of a given cell subpopulation.

The term "previously determined criterion" as used herein relates to a criterion which was established on the basis of one or more sample parameters, in the case of the present invention especially based on cell volume parameters, cell number parameters and cell density parameters. The criterion is determined on the basis of a comparison between infected blood samples and corresponding values of normal blood samples, for example, for the experimental investigations on which the present invention is based, a comparison of 204 *P. falciparum* infected blood samples with corresponding values of 3240 normal blood samples was carried out.

By combination and assessment of sample parameters of polymorphonuclear neutrophil granulocytes (cell volume and cell density) and additionally, by including the thrombocyte number and also the distribution of the cell density of the thrombocytes in the sample, in accordance with the invention unexpectedly high values for the sensitivity and specificity of the detection method were able to be obtained. As is presented in the examples, success rates for specificity values of 99% and sensitivity values of 98% have been achieved here. This means that with full-coverage automated blood examinations the number of false-positive or false-negative diagnosis results could be reduced to a previously unknown extent. This means great progress in respect of a secure *plasmodium* infection diagnosis, especially malaria diagnosis and in countries which are affected by a high prevalence/incidence of malaria infections will lead to a marked improvement of the overall state of health and timely and sensible medical action.

In an embodiment of the inventive method the parameters are determined by scattered light measurement. By contrast with impedance measurement, scattered light measurement involves, as stated above ("optical methods") a method in which laser light is used, wherein the blood samples (cell by cell) are passed through the laser light and the deflection of the laser beams can be detected by a suitable facility. The method performed using the laser beams is explained in the enclosed FIG. 1. In this method the light beams scattered by the individual cells are detected in various angular ranges (low angle and high angle), which respectively allow information to be obtained about volume (low angle) and density (high angle). In accordance with the invention an angle of around 2° to 3° deviation from the laser light axis is referred to as a "low angle", an angle of around 5° to 15° as a "high angle". It has transpired that scattered light measurement is superior to impedance measurement in respect of lower susceptibility to errors of the measurement results.

In an embodiment the *plasmodium* infection involves an infection with *P. ovale* (Malaria tertiana), *P. vivax* (Malaria tertiana), *P. malariae* (Malaria quartana) or *P. falciparum* (Malaria tropica). The inventive detection method can be used equally for these *plasmodium* infections.

In an embodiment, in addition to the above method steps, a spherization and differential analysis of the reticulocytes and erythrocytes in the patient blood sample is additionally carried out by scattered light measurement. Here too a differential analysis is involved, wherein the parameters ultimately to be evaluated involve the cell volume, the cell density and also the hemoglobin content of the cells and of the reticulocyte portion. Reticulocytes involve young red blood corpuscles which, by contrast with the erythrocytes, still contain RNA themselves and can be differentiated by this method.

The spherization of the erythrocytes or reticulocytes is necessary in order to convert the blood cells independently of their original form into a form able to be evaluated with the scattered light measurement. For this purpose the blood sample has a reagent added to it which leads to a spherization of the reticulocytes and erythrocytes. Typical reagents are disclosed in U.S. Pat. Nos. 5,045,472, 5,284,771, 5,633,167 and also U.S. Pat. No. 6,114,173. For example U.S. Pat. No. 5,045,472 discloses a reagent mixture comprising an isotonic aqueous solution, a spherization means (for example a detergent such as alkali metal salts of an alkyl sulfate) and also a protein, which reversibly binds the spherization means.

By including the reticulocytes and a erythrocytes in the inventive detection method specificity and sensitivity can be further increased. The ratio of reticulocytes to erythrocytes is an important indicator of the presence of a *plasmodium* infection in blood. The higher the ratio of reticulocytes, i.e. younger, more immature erythrocytes in relation to mature erythrocytes, the higher is the probability of the presence of a *plasmodium* infection.

In a further embodiment, after a peroxidasic coloring of all leukocytes in the blood sample, a differential analysis is carried out by scattered light measurement and absorption.

The peroxidasic coloring is usually undertaken by cellular peroxidasic activity after conversion with 4-Chloro-1-naphthol. 4-Chloro-1-naphthol serves here as a substrate which makes it possible for hydrogen peroxide to form a dark precipitate at endogen locations of the peroxidasic activity in the granula of the leukocytes. In a scattered light measurement the cells with a small or moderate peroxidasic activity will then absorb less light, while cells with a high peroxidasic activity will absorb more light.

In a further embodiment, after the peroxidasic coloring, as previously explained, the volume distribution of the neutrophil granulocytes is additionally measured. It is also true here that the greater the volume distribution of the neutrophil granulocytes is, the greater is the probability of the presence of a *plasmodium* infection in the patient blood sample.

In a further embodiment the standard deviation of the volume distribution of all leukocytes after peroxidasic coloring is used as an additional parameter. The greater the standard deviation of the volume distribution of all leukocytes is, the greater is the probability of the presence of a *plasmodium* infection.

In an embodiment the determination in step a), i.e. the performing of a differential analysis of the polymorphonuclear neutrophil granulocytes in the sample after lysis of at least the eosinophils and neutrophils, but not of the basophil leukocytes (BASO lysis reagent), is undertaken by a suitable lysis reagent. Here too the presence of a wide volume or density distribution is a symptom of the presence of a *plasmodium* infection. Mixtures based on phatalic acids and detergents have proved to be advantageous here as lysis reagents, for example such a reagent can contain hydrochloric acid, phthalic acid, a surfactant and also optionally a conservation means. The ratio of phthalic acid and hydrochloric acid is around 2.5:1 here (based on their concentration in mmol/l. Through this reagent the red blood corpuscles, the thrombocytes, and all leukocytes (except for the basophil granulocytes) are lysed. The *plasmodium*-specific prediction value can also be increased by this method.

In a further embodiment, after a specific lysis of all cells except for the basophil leukocytes, the non-specific portion from the scattered light diagram (low angle and high angle distribution) is determined. The greater this portion is the greater is the probability that a *plasmodium* infection is present.

The determination steps a), b) and c) performed in the inventive detection method are, as explained above, predictive for the presence of a *plasmodium* infection. The term "low" values in the context of the present invention means a lower value of the determination performed in the individual case compared to the standard values obtained for normal patient samples (i.e. non-infected patient samples).

By contrast, the additional inclusion of the parameters which are obtained by peroxidasic coloring as well as in determination of the volume distribution of the neutrophil granulocytes as well as the standard distribution of the volume distribution of all leukocytes, as well as the determination of the unspecific portion from the scattered light diagram after specific lysis of all cells, means that the higher the values are, the higher is the probability that a *plasmodium* infection is present.

Figure 1:
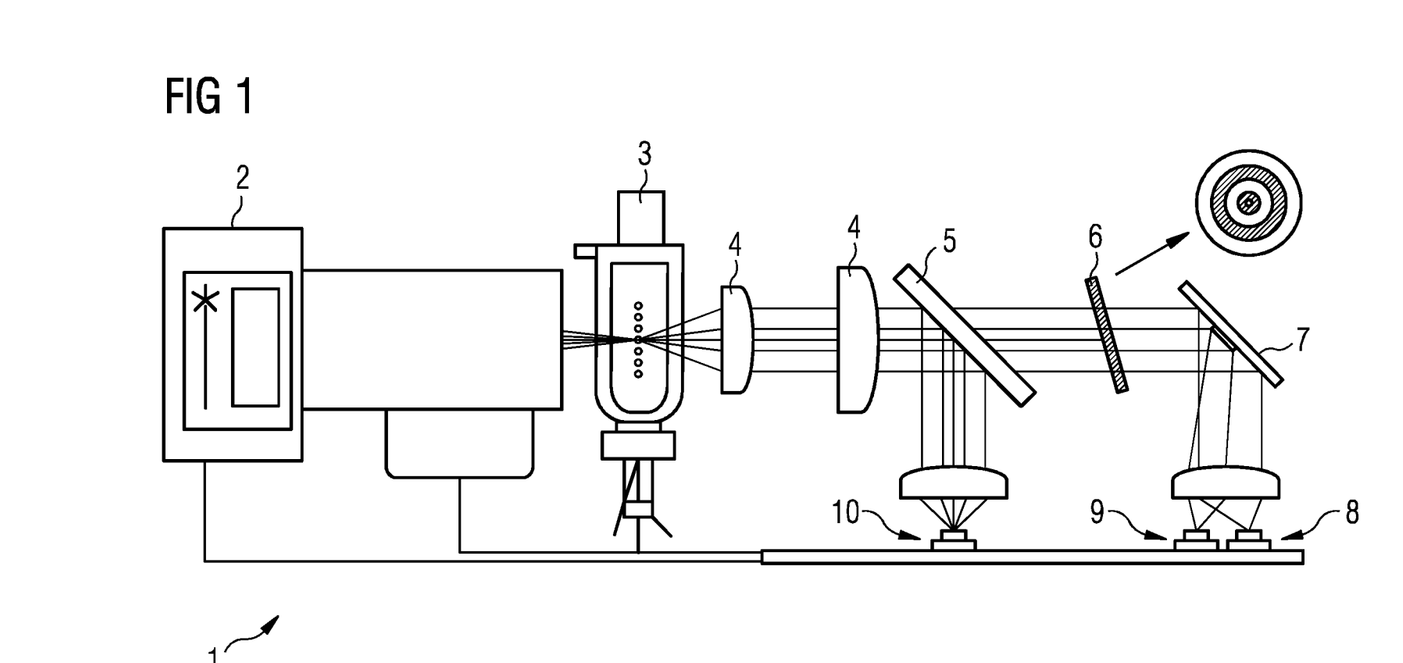
FIG. 1 shows a schematic diagram of a flow cytometry facility 1 for performing the inventive method.

Embodiments of the inventive method are also described in greater detail below, which refer to the enclosed figures, in which:

FIG. 1 shows a schematic diagram of a flow cytometry facility 1 for performing the inventive method. The flow cytometry facility 1 includes a laser 2, a sensor module 3, optical lenses 4, a semi-transparent mirror 5, an aperture 6, a reflector 7, and sensors 8, 9, 10.

Figure 2:
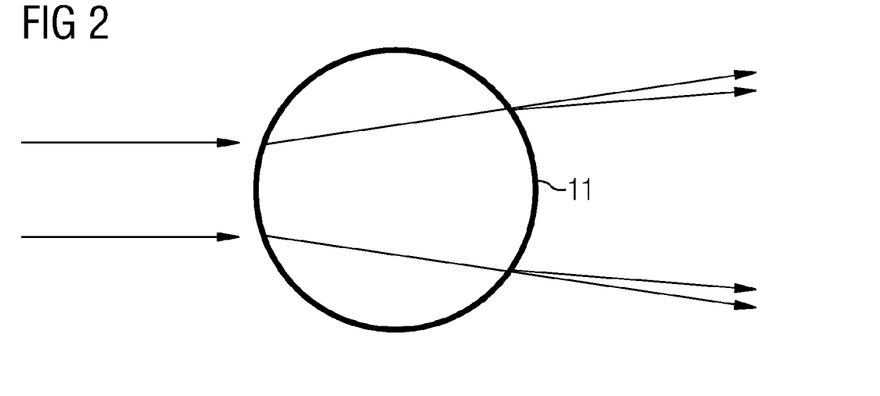
FIG. 2 shows a schematic diagram of the large angle scattered light on the basis of a red blood cell.

FIG. 2 shows a schematic diagram of the large angle scattered light on the basis of a red blood cell 11, which correlates with the granularity and density of the cell and is measured in a typical range of 5° to 15°. This corresponds to the determination of the cell density.

Figure 3:
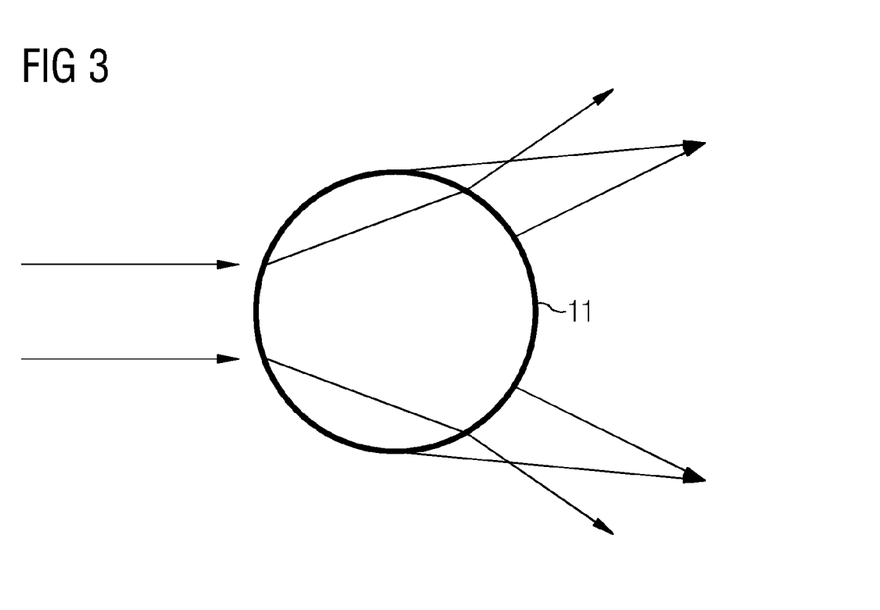
FIG. 3 shows the determination of the cell volume.

FIG. 3 shows the determination of the cell volume (or of the cell size) of the cell 11 in the low angle scattered light range (2° to 3°).

Figure 4:
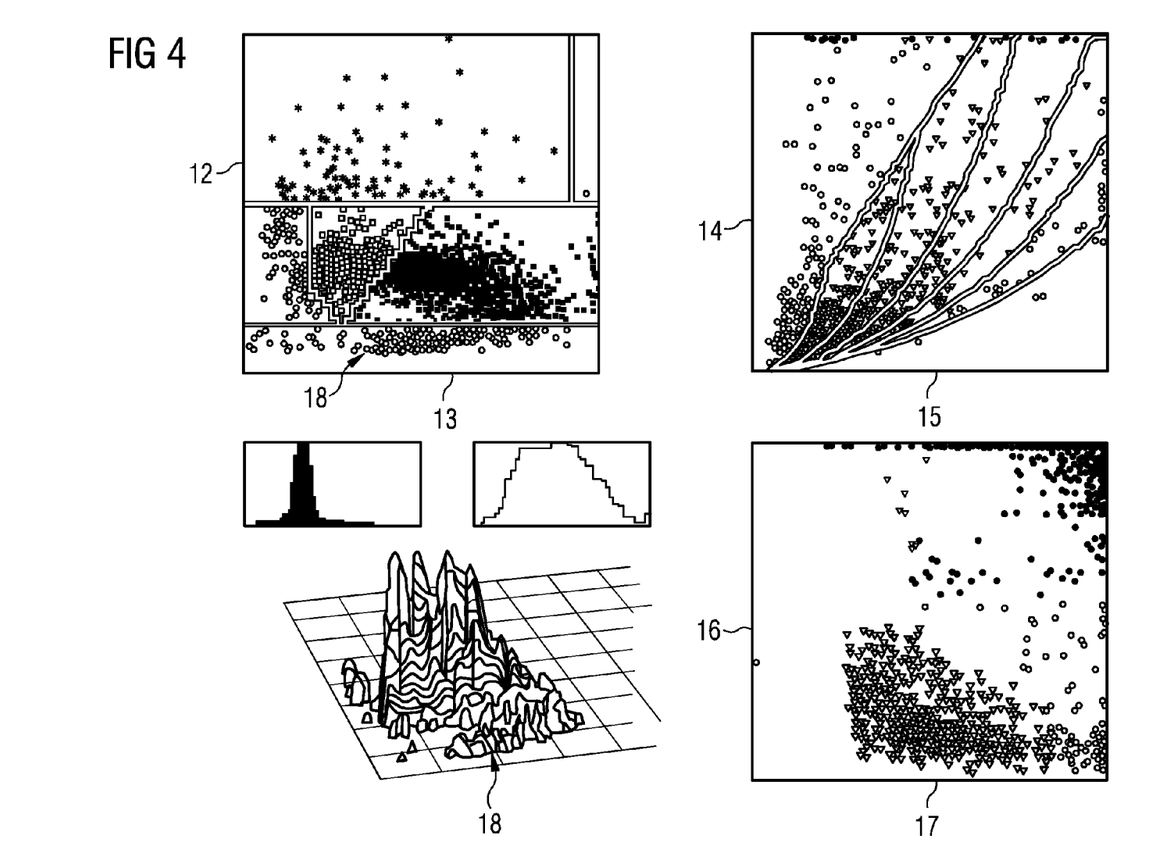
FIG. 4 shows scattered light diagrams executed with the device ADVIA 2120i.

FIG. 4 shows scattered light diagrams executed with the device ADVIA 2120i, which shows the typical displacement of the volume 16 and the density 17 for thrombocytes and polymorphonuclear leukocytes (PMNx) for malaria-infected blood samples. FIG. 4 includes a scattered light diagram showing Baso volume 12, Baso configuration 13, large-angle scatter PLT 14, small angle scatter PLT 15, and a non specific component from the scattergram 18.

Figure 5:
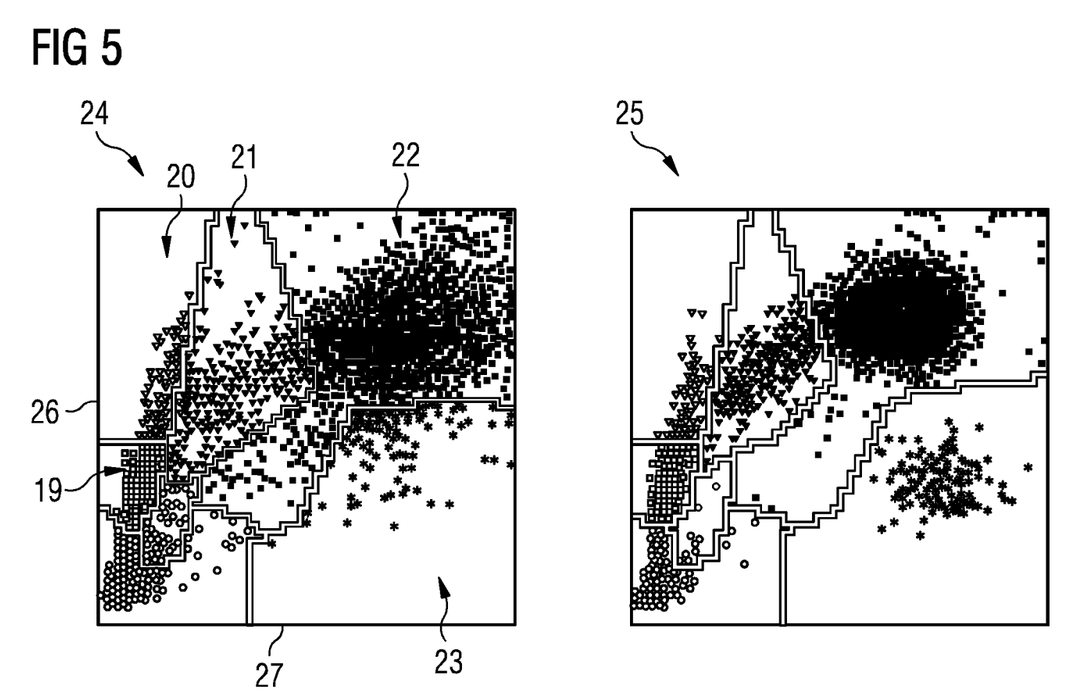
FIG. 5 shows the results of an analysis after peroxidasic coloring with the device ADVIA 2120i.

FIG. 5 shows the results of an analysis after peroxidasic coloring with the device ADVIA 2120i, which shows examples of the volume and density distribution (PEROX Y 26 or PEROX X 27) between a malaria-infected sample 24 and a normal sample 25. "PEROX Y" 26 refers to the width of the peroxidasic-negative populations along the Y axis. With a malaria sample this appears longer by comparison with a normal sample. The results for the malaria sample 24 have a more diffuse effect than the normal sample 25, which is attributable to the greater volume distribution 26 and density distribution 27. In FIG. 5, lymphocytes 19, large unstained cells 20, monocytes 21, neutrocytes 22, and eosinophillic leukocytes 23 are represented.

The performance of the inventive method is shown by way of example below as well as two algorithms which, on the basis of the inventive method, make possible the evaluation of the determined parameters and a prediction of a *plasmodium* infection with high specificity and sensitivity. The measurements are performed with the ADVIA 2120i system from SIEMENS AG.

TABLE 1

The following abbreviations are used:

| Parameter | Description |
|---|---|
| PMNx | Density distribution of the polymorphonuclear leukocytes |
| MPC | Distribution of the cell density of the thrombocytes |
| PLT | Total quantity of thrombocytes in the blood sample |
| PLT mode | Device setting of ADVIA 2120i |
| % Baso Noise | Unspecific portion from the scattered light diagram (small and large angle distribution) after specific lysis by BASO lysis reagent |
| % Abnorm | Standard deviation of the cluster distribution of all leukocytes |
| PEROX Y Sigma | Volume distribution of the neutrophil granulocytes after peroxidasic coloring |

In accordance with a first inventive evaluation the following algorithm 1 was produced for a detection method for a malaria infection with high specificity:

PLT×MPC/100<47 and

PMNx+0.1635×(PLT×MPC/100)<33

On the basis of this algorithm it can be clearly seen (see below) that the setting of the results of a differential analysis of the polymorphonuclear neutrophil granulocytes in relation to one another in relation to the distribution of the cell density (PMNx) with the number of thrombocytes and the distribution of the cell density of the thrombocytes in the sample, possibly with the inclusion of further sub algorithms (1b and 1c) leads to a very high specificity.

With the inclusion of the further sub algorithms

PLT mode−30×% Baso Noise<27 and also

Perox Y Sigma+12/70×% Abnorm>12 a test specificity for malaria of 99% and a sensitivity of 76.5% was produced.

Algorithm 1 can thus advantageously be used in countries with a high prevalence of malaria.

For countries with a lower malaria prevalence the following algorithm 2 would make sense:

| | |
|---|---|
| PMN peak+14/140×(PLT×MPC)/100<34 | 2a. |
| Baso Noise>0.074 | 2b. |
| PLT Mode+25×% Baso Noise<45 | 2c. |
| Perox Y Sigma>6.6 | 2d. |

The observed specificity amounted to 90.2%, the sensitivity to 98.9%. In other words an extremely high sensitivity can be achieved by the algorithm 2.

Thus almost all malaria positive samples can be detected by the algorithm 1 in a large sample population, while algorithm two is especially suitable for screening examinations. A combination of the two algorithms can additionally be of advantage.

The invention claimed is:

1. A method for detecting an indication of a possible *plasmodium* infection in a patient blood sample, the method comprising the steps of:
    a) obtaining a blood sample from a patient suspected of having a possible *plasmodium* infection;
    b) performing a differential analysis of polymorphonuclear neutrophil granulocytes in the sample and determining a distribution of cell volume and cell density by scattered light measurement using a hematology system;
    c) coloring the neutrophil granulocytes and determining the volume distribution of the colored neutrophil granulocytes;
    d) determining a number of thrombocytes in the sample by scattered light measurement using a hematology system;
    e) determining a distribution of cell density of the thrombocytes in the sample by scattered light measurement using a hematology system;
    f) obtaining sample parameters from the values determined in steps b)-d), wherein the sample parameters include the number of thrombocytes in the blood sample (PLT), the distribution of cell density of the thrombocytes in the blood sample (MPC), and the distribution of cell density of polymorphonuclear neutrophil granulocytes in the blood sample (PMNx);
    g) evaluating the parameters in relation to a prespecified criterion, wherein, if the criterion is fulfilled, presuming a possible *plasmodium* infection is present, and wherein the criterion is expressed as (PLT×MPC)/100 <47 and PMNx +0.1635×(PLT×MPC)/100 <33; and
    h) diagnosing a patient as being possibly infected with *plasmodium* if the patient blood sample indicates the presence of a possible *plasmodium* infection.

2. The method as claimed in claim 1, wherein the *plasmodium* infection involves an infection with *Plasmodium falciparum, Plasmodium vivax, Plasmodium ovale, Plasmodium malariae* or *Plasmodium knowlesi*.

3. The method as claimed in claim 1, wherein an additional spherization and differential analysis of reticulocytes and erythrocytes is performed by scattered light measurement and absorption measurements.

4. The method as claimed in claim 1, wherein, after the coloring of all neutrophil granulocytes in the sample, a differential analysis is undertaken by scattered light measurement and absorption.

5. The method as claimed in claim 4 wherein the coloring is performed with 3-chloro-1-naphthol as a substrate.

6. The method as claimed in claim 1, wherein the standard deviation of the volume distribution and absorption distribution of all neutrophil granulocytes after the coloring are used as additional parameters.

7. The method according to claim 6 wherein an increase of the parameters is predictive for the presence of a possible *plasmodium* infection.

8. The method as claimed in claim 1, wherein the determination of a distribution of cell volume and cell density in step b) includes using a suitable lysis reagent to lyse eosinophils and neutrophils but not basophil leukocytes and measuring the cell volume and cell density of the unlysed basophil leukocytes.

9. The method as claimed in claim 1, wherein the determination of a distribution of cell volume and cell density in step b) includes performing a specific lysis of all cells except for basophil leukocytes, coloring the unlysed basophil leukocytes instead of step c), and measuring the cell volume and cell density of the unlysed basophil leukocytes from a scattered light diagram created using low and high angle scattering.

10. The method as claimed in claim 1, which is performed by an automated cell counting device.

* * * * *

UNITED STATES PATENT AND TRADEMARK OFFICE
CERTIFICATE OF CORRECTION

PATENT NO. : 9,605,293 B2
APPLICATION NO. : 13/996948
DATED : March 28, 2017
INVENTOR(S) : Oliver Hayden and Jan Van den Boogaart It is certified that error appears in the above-identified patent and that said Letters Patent is hereby corrected as shown below:

On the Title Page

Item (75), 2nd inventor please delete "Jan Van den Boogaart, Someren (NE)" and insert --Jan Van den Boogaart, Someren (NL)--.

Signed and Sealed this
Ninth Day of January, 2018

Joseph Matal
*Performing the Functions and Duties of the
Under Secretary of Commerce for Intellectual Property and
Director of the United States Patent and Trademark Office*